(12) United States Patent
Schlaudraff (10) Patent No.: US 9,719,894 B2
(45) Date of Patent: Aug. 1, 2017

(54) SPECIMEN COLLECTOR FOR COLLECTING A LASER MICRO-DISSECTATE

(71) Applicant: LEICA MICROSYSTEMS CMS GMBH, Wetzlar (DE)

(72) Inventor: Falk Schlaudraff, Butzbach/Nieder-Weisel (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 0 days.

(21) Appl. No.: 14/402,122

(22) PCT Filed: May 22, 2013

(86) PCT No.: PCT/EP2013/060500
§ 371 (c)(1),
(2) Date: Nov. 19, 2014

(87) PCT Pub. No.: WO2013/174862
PCT Pub. Date: Nov. 28, 2013

(65) Prior Publication Data
US 2015/0125363 A1    May 7, 2015

(30) Foreign Application Priority Data

May 24, 2012    (DE) .................. 10 2012 208 737

(51) Int. Cl.
*B01L 3/00*    (2006.01)
*G01N 1/28*    (2006.01)

(52) U.S. Cl.
CPC ........ *G01N 1/286* (2013.01); *B01L 3/502715* (2013.01); *B01L 3/502738* (2013.01);
(Continued)

(58) Field of Classification Search
CPC ..... B01L 2400/0406; B01L 2400/0403; B01L 2400/04; B01L 2400/00; B01L 2400/0487;
(Continued)

(56) References Cited

U.S. PATENT DOCUMENTS 5,757,482 A    5/1998 Fuchs et al.
5,998,129 A    12/1999 Schuetze et al.
(Continued)

FOREIGN PATENT DOCUMENTS

DE    10018253 C2    10/2001
DE    10057292 C2    2/2003
(Continued)

OTHER PUBLICATIONS

Written Opinion of the International Searching Authority English Translation, PCT/EP2013/060500, pp. 1-6, obtained on Sep. 1, 2015.*

(Continued)

*Primary Examiner* — Christine T Mui
(74) *Attorney, Agent, or Firm* — Leydig, Voit & Mayer, Ltd.

(57) ABSTRACT

A laser microdissectate specimen collector for a laser microdissection device includes a collecting chamber configured to receive a dissectate. The collecting chamber has, on a specimen side, an opening open to the environment for receiving the dissectate. The collecting chamber also has a first valve. The first valve, in a closed state thereof, forms a closure of the collecting chamber opposite to the opening for retaining the dissectate. A capillary line is connected downstream of the first valve to the collecting chamber such that the capillary line is configured to transport the dissectate out of the collecting chamber.

26 Claims, 8 Drawing Sheets

(52) U.S. Cl.
CPC . B01L 3/502784 (2013.01); *B01L 2200/0631* (2013.01); *B01L 2200/0673* (2013.01); *B01L 2200/10* (2013.01); *B01L 2300/0681* (2013.01); *B01L 2300/0816* (2013.01); *B01L 2300/0864* (2013.01); *B01L 2400/0406* (2013.01); *G01N 2001/2886* (2013.01)

(58) Field of Classification Search
CPC ........... B01L 2400/0475; B01L 3/0262; B01L 3/0241; B01L 3/302; B01L 3/00
USPC .................. 422/507, 504, 502, 501, 500, 50
See application file for complete search history.

(56) References Cited

U.S. PATENT DOCUMENTS

| | | | |
|---|---|---|---|
| 6,193,647 B1 * | 2/2001 | Beebe | A61B 17/435 600/33 |
| 6,969,614 B1 | 11/2005 | Liotta et al. | |
| 7,312,085 B2 * | 12/2007 | Chou | B01L 3/502761 422/50 |
| 7,592,139 B2 * | 9/2009 | West | B01L 3/5027 435/287.1 |
| 7,670,559 B2 * | 3/2010 | Chien | B01L 3/502715 422/504 |
| 8,573,073 B2 | 11/2013 | Thalhammer et al. | |
| 8,676,831 B2 * | 3/2014 | Wieser | G06F 17/30398 707/713 |
| 2002/0061261 A1 | 5/2002 | Pfeifer et al. | |
| 2003/0133190 A1 | 7/2003 | Weiss | |
| 2006/0186349 A1 | 8/2006 | Weiss | |
| 2006/0194307 A1 * | 8/2006 | Yasuda | B01L 3/502761 435/288.7 |
| 2007/0095669 A1 | 5/2007 | Lau et al. | |
| 2008/0194011 A1 | 8/2008 | Wesner | |
| 2013/0234015 A1 | 9/2013 | Becker et al. | |

FOREIGN PATENT DOCUMENTS

| | | |
|---|---|---|
| DE | 10329674 A1 | 2/2005 |
| DE | 102005008925 A1 | 9/2006 |
| DE | 102005028062 B4 | 11/2010 |
| DE | 102009016512 B4 | 5/2011 |
| EP | 2083257 A1 | 7/2009 |
| WO | WO 9729354 A1 | 8/1997 |
| WO | WO 2004035210 A2 | 4/2004 |

OTHER PUBLICATIONS

English Translation of WO 97/29354 Description, Diessel et al, Process and Device for Sorting and for Extraction of Biological Objects Arranged on Planar Means, Such as Biological Cells or Cell Organelles, Histological Sections, Chromosome Particles etc. Using Laser Beams, obtained on Sep. 1, 2015, http://translationportal.epo.org, pp. 1-34.*

* cited by examiner

SPECIMEN COLLECTOR FOR COLLECTING A LASER MICRO-DISSECTATE

CROSS-REFERENCE TO PRIOR APPLICATIONS

This application is a U.S. National Phase Application under 35 U.S.C. §371 of International Application No. PCT/EP2013/060500, filed on May 22, 2013, and claims benefit to German Patent Application No. DE 10 2012 208 737.0, filed on May 24, 2012. The International Application was published in German on Nov. 28, 2013 as WO 2013/174862 under PCT Article 21(2).

FIELD

The present invention relates to a laser microdissectate specimen collector for a laser microdissection device and to such a laser microdissection device.

BACKGROUND

In laser microdissection, selected tissue regions or cells are separated out or cut out ("dissected") from microscopic tissue specimens with the aid of a focused laser beam for further analysis.

DE 100 18 253 C2, DE 10 2005 028 062 B4 and DE 10 2005 008 925 A1 by the applicant describe possible methods and systems for laser microdissection employing a microscope.

Capillary-based analytical apparatuses are so far advanced that individual cells or even chromosomes detached from tissue can be transported in droplets or solution through capillary systems, and sorted, analysed and also utilised further after analyses. Capillary-based analytical techniques are used and promoted, for example, by FLUIDIGM and RAINDANCE TECHNOLOGIES.

In order to be able to be analysed using these techniques, the specimens and individual cells must first be separated; this can be effected by fluorescence-based flow cytometry, laser microdissection and transpipetting into an appropriate feed medium for the capillary systems.

Various collectors are available for so-called "dissectates" cut out in the laser microdissection, for example so-called "tube caps", 8-well strips, 8-well strip caps or so-called "lab coat pocket laboratories" (also called "lab on a chip"), for example AmpliGrid devices. After the laser microdissection process, these collectors are removed physically from the dissection machine and further processed separately. As a rule centrifugation and pipetting steps are necessary for this, before the dissectate can be fed in appropriate solution to an analytical method, such as the polymerase chain reaction (PCR), reverse transcription PCR (RT-PCR) or real time or quantitative PCR (rt-/qPCR) or mass spectrometry (MS).

This procedure has the disadvantage that the possibilities for an automated further processing of specimens directly after isolation by means of laser microdissection are severely limited. Furthermore, the necessary complex centrifugation and pipetting steps have a high risk of contamination and specimen loss.

EP 2 083 257 A1 discloses a method and a device for transferring a microscopic, isolated specimen. Here, a nanosuction apparatus is positioned over a specimen which has been cut out of a specimen body on an object table. The nanosuction apparatus actively sucks up the specimen from the object table, before it is swivelled and then blows out the specimen again at a different place. The specimen can thus be transferred, for example, into a reaction vessel. Before the sucking up, however, visual inspection of the specimen is not possible or is at least only inadequate, because this is still surrounded by the remaining specimen body from which it has been cut out.

DE 10 2009 016 512 B4 discloses a laser ablation chamber consisting of a container which can be closed in a gas-tight manner from the top with a cover glass, on the underneath of which the specimen to be analysed is located. The container has a feed line and a removal line for a transporting gas (for example argon). An examination of the specimen is first carried out with a determination of the regions to be removed by means of laser ablation. This examination is carried out with a laser microdissection apparatus utilising the high-resolution lens of such an apparatus. After determination of appropriate regions, these are detached from the specimen by means of laser ablation and transported out of the gas-tight container, for example into an analytical device, such as a mass spectrometer, by feeding in the transporting gas. Further specimen regions can be analysed, depending on the result of the analysis. The known laser microdissection can be employed for this, which allows dissection of specimen sections in the submicron range with high precision. For laser microdissection, the laser ablation chamber described is replaced by conventional specimen holders for laser microdissection.

The object of DE 103 29 674 A1 is to overcome the disadvantages of UV ablation, such as the absorption of UV radiation in biological tissue or the low cutting quality. For cutting biological material, the use of ultra-short laser pulses in the pico- or femtosecond range with secondary frequencies of at least 1,000 Hz at a laser wavelength of greater than 400 nm (near infra-red) is proposed here, the laser being focused on the specimen in order to generate high intensities of at least $10^{12}$ W/cm$^2$ there. By this means a so-called non-resonant multiphoton absorption is achieved, which generates a plasma for the cutting action. In one embodiment the biological material cut out is separated from the surrounding specimen by the gravitational effect and falls onto a cover glass coated with lysine. In this procedure, for example, the specimen with the film carrying it is applied to the underside of a glass window. A silicone ring joins the glass window to the lysine-coated cover glass. The biological material cut out can be either sucked off, for example by inserting two cannulas through the silicone ring, or flushed out by means of hydrodynamic flow and collected by means of a sterile filter. The upper glass window, the silicone ring and the lower cover glass for collecting the material cut out overall form a closed sterile chamber.

SUMMARY

In an embodiment, the present invention provides a laser microdissectate specimen collector for a laser microdissection device including a collecting chamber configured to receive a dissectate. The collecting chamber has, on a specimen side, an opening for receiving the dissectate. The collecting chamber also has a first valve. The first valve, in a closed state thereof, forms a closure of the collecting chamber opposite to the opening for retaining the dissectate. A capillary line is connected downstream of the first valve to the collecting chamber such that the capillary line is configured to transport the dissectate out of the collecting chamber.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

In an embodiment, the present invention renders possible an automated specimen processing after laser microdissection has taken place, in particular with the possibility of visualisation or detection of the dissectate.

The laser microdissectate specimen collector according to an embodiment of the invention has an inspectable collecting chamber for receiving a dissectate, wherein this collecting chamber has on the specimen side an opening substantially open to the environment for receiving the dissectate. The collecting chamber furthermore has a first valve which in the closed state forms a closure (or base), facing away from the specimen, of the collecting chamber for in particular temporary retention of the dissectates. A capillary line is arranged downstream of the first valve, and is connected to this collecting chamber for transporting the dissectate (with the valve open) out of the collecting chamber.

In the following, the terms "downstream" and "upstream" are intended to relate to a direction of flow which is directed from the specimen-side opening in the collecting chamber via the first valve in the direction of the capillary line, so that the direction of flow consequently describes the transport path of the dissectate.

"An opening which is substantially open to the environment" in the collecting chamber is to be understood as meaning that the collecting chamber is not sealed off so as to be isolated from gas or liquid.

An embodiment of the present invention has the advantage that the specimen collector according to the invention can collect a specimen which has been cut out (a dissectate), can initially retain it on the base formed by the closed first valve and can then guide it further to and through the capillary line, without a manual working step being necessary. Between the collection and the further guiding of the dissectate, this can optionally be visually inspected or detected. After being passed on, the dissectate can be fed to the analysis. In particular, the specimen collector does not have to be removed and/or inclined manually in order to be passed on. An automation of the specimen processing is rendered possible in this manner, which improves working convenience and reduces working times. Furthermore, contamination and/or loss of material promoted by manual working steps can be avoided or at least reduced. In particular, the specimen can be protected directly after the dissection process by using a suitable buffer or solvent for flushing and can be fed to the analysis.

The collecting chamber can be a part of the inner surface of the specimen collector. The connection of the collecting chamber to the capillary line can be in the form of a direct connection which includes the first valve. The collecting chamber and capillary line here can be produced as segments of a common, single component, for example made of glass or plastics material. Such segments can follow one another, or the component can have a (valve) section arranged between the two said segments. Alternatively, the collecting chamber and the capillary line can be present as separate components or parts of separate components which are connected to one another directly or via one or more connection part(s) (first valve). The separate components can consist of the same material or the same materials. Alternatively, at least one of the components can contain at least one material which is not contained in the other component.

The capillary line can be a capillary or a tube.

The collecting chamber can serve, for example, to collect a plurality of dissectates, in order then to pass them together via the first valve through the capillary line and to make them available to further reaction processes from there. Such a collecting chamber moreover allows or facilitates an addition of a transporting/carrier substance, such as a liquid, for example for flushing out the dissectate through the discharge line.

In this context a second valve, for example, can be provided, which closes or opens the collecting chamber as required such that a dissectate or other material can fall into the collecting chamber only when the valve is open. In particular, after the dissectate has been collected, penetration of foreign material, such as dirt particles, into the collecting chamber can thus be prevented by closing the second valve. In the closed state the second valve then forms a specimen-side closure ("lid") of the collecting chamber.

Transporting of the dissectate from the collecting chamber and through the capillary line can be controlled by the first valve. The point in time at which a dissectate is guided through the capillary line and fed to the further processing or analysis of the specimen can be controlled in this way. For example, after being cut out and before it is transported out of the collecting chamber, the dissectate can first be inspected visually by a user.

In a preferred embodiment the collecting chamber and/or the capillary line can have at least one injector using which a liquid or other transporting substance can be fed in. By this means it is possible, for example, to add a liquid for transporting the dissectate through the capillary line. Alternatively or in addition, a substance addition suitable for the further specimen processing can be effected, for example a suitable buffer, a solvent, a micelle-forming liquid or the like. Both types of added substances are to be combined under the term "carrier substance" in the following.

If the specimen collector comprises a collecting chamber with two valves, as described above, it is advantageous if an injector is arranged between the valves. This allows the collecting chamber to be closed before a substance is added, so that, for example, no odours or vapours of the substance can emerge or the substance is not contaminated.

The specimen collector can comprise a dispenser which is preferably arranged between the collecting chamber and the capillary line. The dispenser is preferably arranged downstream of the collecting chamber.

Such a dispenser renders it possible to enclose the dissectate in a drop of liquid. Individual drops can then preferably be sorted in the discharge line. For example, drops which contain a dissectate can be separated from other drops. Drops without dissectate can then be fed, for example, to a reutilisation or further utilisation (for example by re-injection with an injector of the specimen collector), whereas drops with dissectate can be passed to analytical operations.

Tiny volumes of liquids can be transported with a capillary line. The capillary line can have a branching. The branching can be constructed as a sorting intersection at which drops with dissectate can be automatically separated (for example by means of an electrical field gradient) from drops without dissectate. By this means the concentration of dissectates in an analysis solution can be increased and the analysis can thus be improved, for example by means of DNA enrichment. If a sorting intersection is used, one removing capillary line can serve to transport dissectate, while another removing capillary line passes the carrier substance back to a reservoir, which substance can then be fed by means of a pump to the collecting chamber, for example via an injector.

In an expedient embodiment, an inspectable outlet device can be arranged upstream of the opening in the collecting chamber, the outlet of which device is connected to the opening in the collecting chamber. In this case the dissectate does not fall directly into the collecting chamber, but falls first into the outlet device, in which it can be inspected, for example visually or with a camera. Via the outlet of the outlet device the dissectate then passes through the opening in the collecting chamber into said chamber.

In a preferred embodiment the outlet device comprises a flushing and/or discharge or suction device. The flushing and/or discharge or suction device can serve to convey the dissectate reliably from the outlet device into the capillary line. The point in time at which the dissectate is transported out of the collecting chamber can thus also be controlled.

In the case of a flushing device, this can be set up to moisten the outlet device before the dissectate falls in and/or continuously and in this way to facilitate transporting of the dissectate which has fallen in. Alternatively, the flushing device can be set up to feed liquid into the collecting device only after the dissectate has been collected, which renders possible a preceding visualisation of the dissectate. The feeding in here can be activated automatically after a predetermined period of time or manually by a user. In this manner on the one hand the user is given time to inspect the dissectate visually before it is flushed into the capillary line, and on the other hand several dissectates can first be collected in the collecting device before they are flushed together into the capillary line.

In an embodiment comprising in particular a flushing device, the outlet device is preferably configured as a collecting area demarcated by raised side edges. By this means the liquid fed in can be collected and the flow direction of the liquid can be controlled by inclining the collecting area with respect to the horizontal. In particular, the dissectate can be flushed into the opening in the collecting chamber in a targeted manner.

In a particularly advantageous embodiment, downstream of the first valve a filter is arranged after this valve, the filter being designed such that it allows the dissectate to pass. The filter is arranged in particular either directly after the first valve before the capillary line or in the capillary line itself. Dissectate passing through the filter is transported further through the capillary line.

The filter can be permeable in particular to the above-mentioned carrier substance, while other, in particular solid, substances foreign to the dissectate are retained. Such substances foreign to the dissectate include, in particular, membrane fragments. In laser microdissection, as a rule so-called membrane microscope slides are used. The material to be dissected is applied to a suitable (as a rule UV laser-absorbing) membrane, the laser of the laser microdissection system also cutting the membrane together with the specimen. The dissectate is consequently completely separated physically from the overall combination of membrane and surrounding specimen. As a result, the extracted specimen (dissectate) is still joined to the similarly extracted membrane (membrane fragment). Membrane fragments can block the capillary lines of the specimen collector and/or influence subsequent reactions.

In the following it is to be assumed that such a described filter is arranged directly behind the first valve of the collecting chamber before the capillary line. The following method can be employed to separate the dissectate from the membrane fragment: the dissected specimen is collected in the collecting chamber, where the dissectate can optionally be inspected. Lysis buffer which separates the dissectate from the membrane fragment is added to the collecting chamber via an injector. The specimen may also be completely lysed/digested by the lysis buffer or digestion enzymes in the lysis buffer, so that the constituents of the formerly solid specimen are in solution (lysate), while the membrane retains its originally solid form. By opening the first valve the (lysed) dissectate passes through the filter into the capillary system, while the co-dissected membrane fragment is retained by the filter.

There are various possibilities for cleaning the filter of membrane fragments: first, the complete collecting chamber with valve(s) and filter can be exchanged and replaced by a new one. Alternatively, only the filter can be exchanged and replaced by a new one. In addition or alternatively, before exchanging the filter or complete collecting chamber (or also to avoid such an exchange), it is possible to flush the filter. For this, for example, the filter can be flushed out in the opposite direction with the first valve open, as a result of which membrane fragments pass into the collecting chamber. The membrane fragments can then be sucked off, for example by means of an injector (or by means of the injector already arranged there).

In a preferred embodiment the specimen collector according to the invention is included in a laser microdissection device. This device furthermore comprises a laser light source for generating a laser beam, a deflecting device for deflecting the laser beam, a objective lens as a focusing lens and a microscope stage for accommodating a microscope slide. The laser beam is focused on the specimen on the microscope slide by means of the objective lens. By means of the deflecting device the laser beam is guided along a cutting line within the specimen. The specimen collector is preferably fixed under the microscope slide and aligned such that a dissectate cut out by the laser beam falls into the collecting chamber (or an upstream outlet device) of the specimen collector.

Such a laser microdissection device comprises a microscope, wherein means are provided for coupling the laser beam into the microscope beam path. This can be a beam splitter which reflects the laser wavelengths while being transparent to the observation wavelengths of the microscope. Optical components (lenses etc.) can furthermore be provided for coupling in the laser beam. Overall, it is expedient to use a incident light device for coupling in and focusing the laser beam through the objective lens onto the specimen. The laser beam then passes through the deflecting device arranged in the incident light device and arrives at the objective lens, which then serves as a focusing lens. The laser beam is focused on the specimen and describes a cutting line on the specimen by means of appropriate deflection by the deflecting device. The specimen is cut along this cutting line, as a result of which the dissectate is formed. Such an arrangement is particularly advantageous, since the specimen can be examined microscopically (for example by means of fluorescence microscopy) and regions of the specimen which are to be dissected can be identified. The operation of laser cutting can furthermore also be observed visually or by means of a camera and optionally controlled, since the microscope stage does not have to be moved during the laser cutting.

With respect to the construction in principle and the mode of functioning of said laser microdissection system which comprises a microscope, reference is expressly made to the patent specification DE 100 18 253 C2. Such a system is advantageous in particular in combination with the specimen collector according to the invention. With respect to details of the system, to avoid repetition the corresponding disclosure of DE 100 18 253 C2 is hereby incorporated by reference herein.

In the context of dissectate processing, it can be ascertained that a predetermined number of dissectates has been collected in the collecting chamber. This can comprise recording of a number of dissection steps performed and comparison of the number recorded with the predetermined number. In this manner, for example, a concentration of dissectates which is required for an analytical operation can be achieved in a solution.

It goes without saying that the features mentioned above and the features still to be explained in the following can be used not only in the particular combination stated but also in other combinations or by themselves without going beyond the scope of the present invention.

Figure 1:
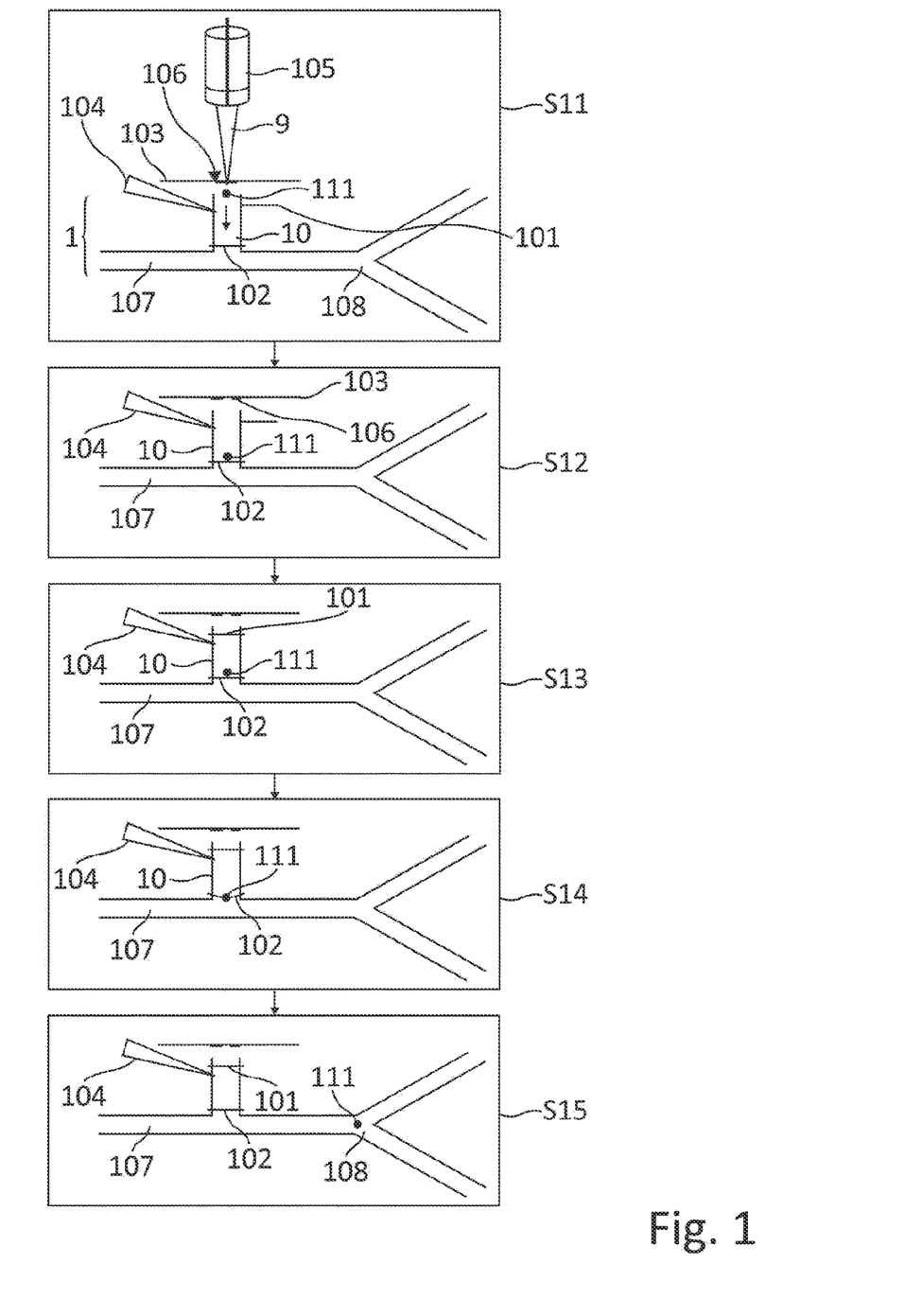
FIG. 1 shows by way of example an embodiment of the specimen collector according to the invention and various method steps during its use.

FIG. 1 shows five steps of a method in which an embodiment of the specimen collector 1 according to the invention is used.

The specimen collector 1 comprises a collecting chamber 10 which, in the case shown, has two valves 101 and 102. The first valve 102 forms in the closed state a closure (base) of the collecting chamber 10 facing away from the specimen 106. In the first step shown, S11, the second valve 101 (lid) is open, and the collecting region is therefore ready to receive a dissectate 111 falling in. On its underside downstream of the first valve 102 the collecting chamber 10 is connected to a capillary line as a discharge line 107 for transporting a dissectate out of the collecting region. Passing on of the dissectate from the collecting region of the collecting chamber 10 into the discharge line 107 is controlled via the valve 102. In the step shown, S11, the valve 102 is closed.

Figure 6:
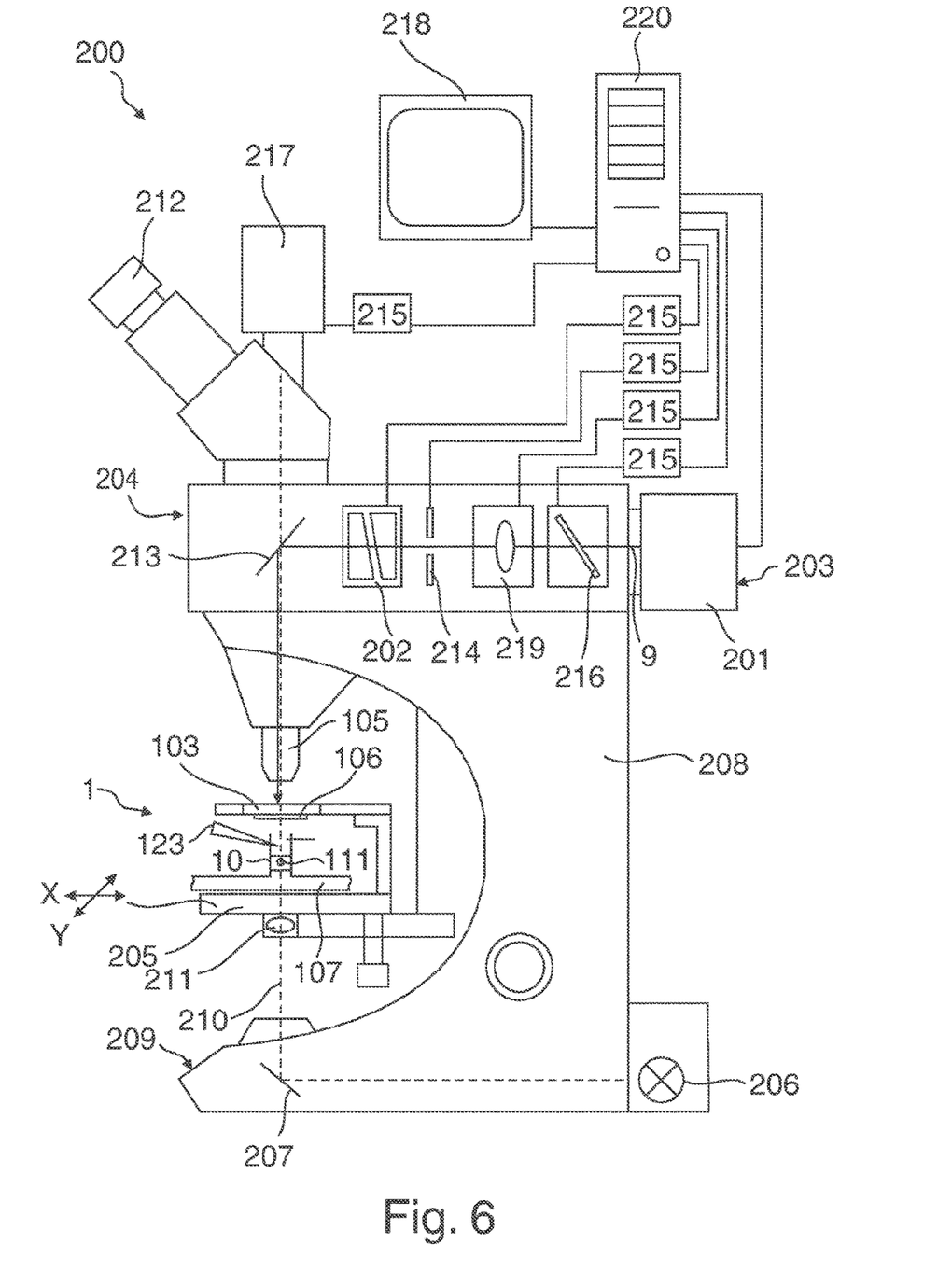
FIG. 6 shows a laser microdissection system with an integrated specimen collector.

The specimen collector 1 is arranged underneath a microscope slide 103 which holds a specimen 106. In step S11 a dissectate 111 is cut out of the specimen 106 by means of a laser beam 9 which is focused by a lens 105 of a microscope. The dissectate cut out falls into the collecting region (that is to say into the collecting chamber) 10 of the specimen collector 1. FIG. 6 explains a possible laser microdissection device in more detail.

When the dissectate has fallen into the collecting chamber (step S12), the upper valve 101 can be closed (step S13). By repeating step S11, further dissectates can be cut out beforehand and received in the collecting chamber 10, until a desired number of dissectates is reached. The lower valve 102 can then be opened in order to render the dissectate accessible directly to the discharge line 107, which can be embedded, for example, in a microfluid capillary system (step S14); preferably, the upper valve 101 is closed here. In step S15 the dissectate 111 shown by way of example arrives at a sorting intersection 108, from where—as explained below—it can be fed to its intended location. During or before or after all steps, a carrier substance, such as a suitable buffer, solvent, micelle-forming liquid or the like, can be added by the optional injector 104. Furthermore, the injector 104 can be used in step S14 for flushing out the dissectate.

Figure 2A:
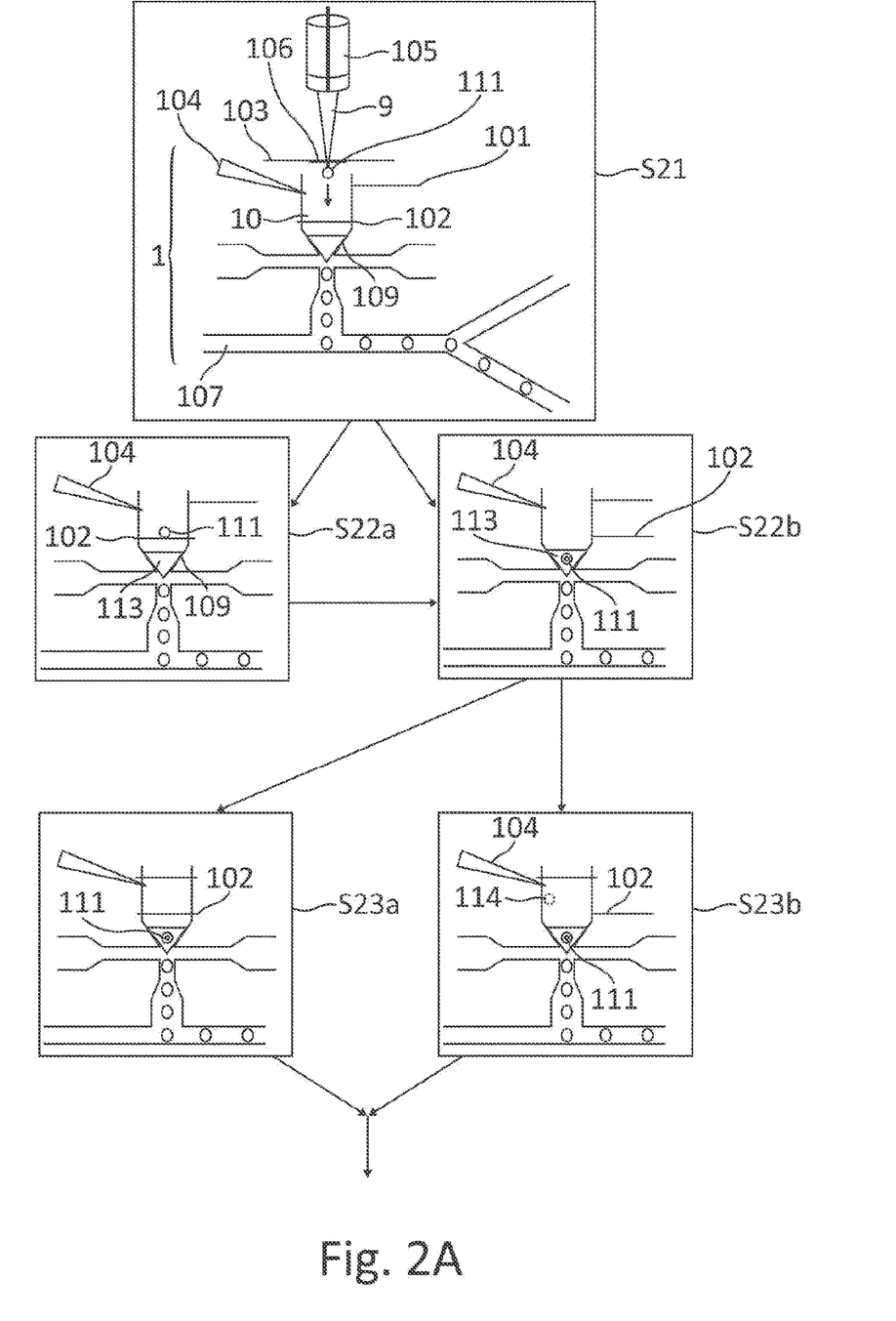
FIG. 2A shows an alternative embodiment of the specimen collector according to the invention and the use thereof.

In addition to the embodiment of a specimen collector just outlined, there is the possibility of combining the collecting chamber 10 with a dispenser 109. Such an embodiment is shown in FIGS. 2A and 2B: in addition to the features shown analogously in FIG. 1, the specimen collector 1 shown in FIGS. 2A and 2B comprises a dispenser 109.

The first step shown, S21, corresponds to step S11 from FIG. 1: a dissectate 111 is cut here out of a specimen 106 and falls into the specimen collector 1, which has a collecting chamber 10. The lower valve 102 can now be either closed (as shown for step S22a) or open (as shown for step S22b). The dissectate 111 is thus either held on the lower valve 102 (step S22a) or mixed with liquid 113 directly in the head of the dispenser 109 (step S22b). In the case of both steps S22a and S22b, an optional addition of a carrier substance before, after and/or during the collecting operation optionally by the injector 104 is possible. If the dissectate corresponding to step S22a is held on or above the lower valve 102, the valve 102 is then opened, so that the dissectate (as shown in step S22b) passes into the dispenser 109.

After step S22b, the lower valve 102 (as shown in step S23a) can be closed again directly. Alternatively (as shown in step S23b), a substance addition 114 can be effected by the injector 104.

Figure 2B:
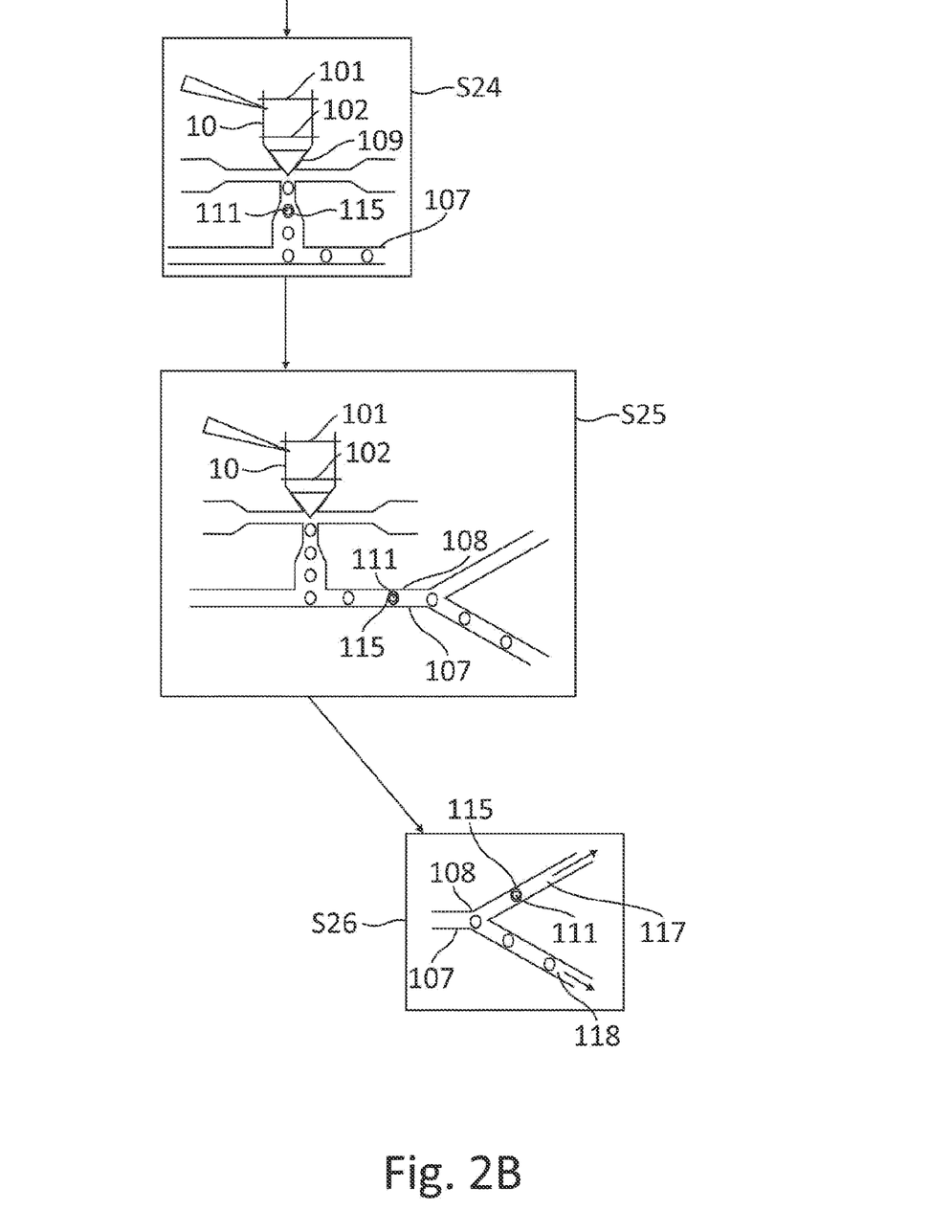
FIG. 2B shows passing on of a dissectate in continuation of the method from FIG. 2A.

According to FIG. 2B, in the next step S24 the dissectate 111 leaves the dispenser 109, as a result of which it is enclosed in a drop 115. In the diagram the lower valve 102 is closed (again) here, but alternatively it could also be open, especially if the preceding step corresponds to step S23b. The drop 115 passes into the capillary line 107.

In step S25 the drop 115 with the dissectate 111 enclosed therein approaches a sorting intersection 108. Drops with dissectates 111 are sorted out there in step S26 by means of an applied electrical field gradient and are fed in a separate capillary 117 to the desired analyses, while drops without dissectates can be sorted into another capillary 118 and recycled. Recycling is optionally renewed injection by the injector. Before the process is repeated, the dispenser 109 possibly has to be topped up, for example by the injector 104. The lower valve 102 is open during this, and the upper valve 101 can likewise be open or also closed.

Figure 3A:
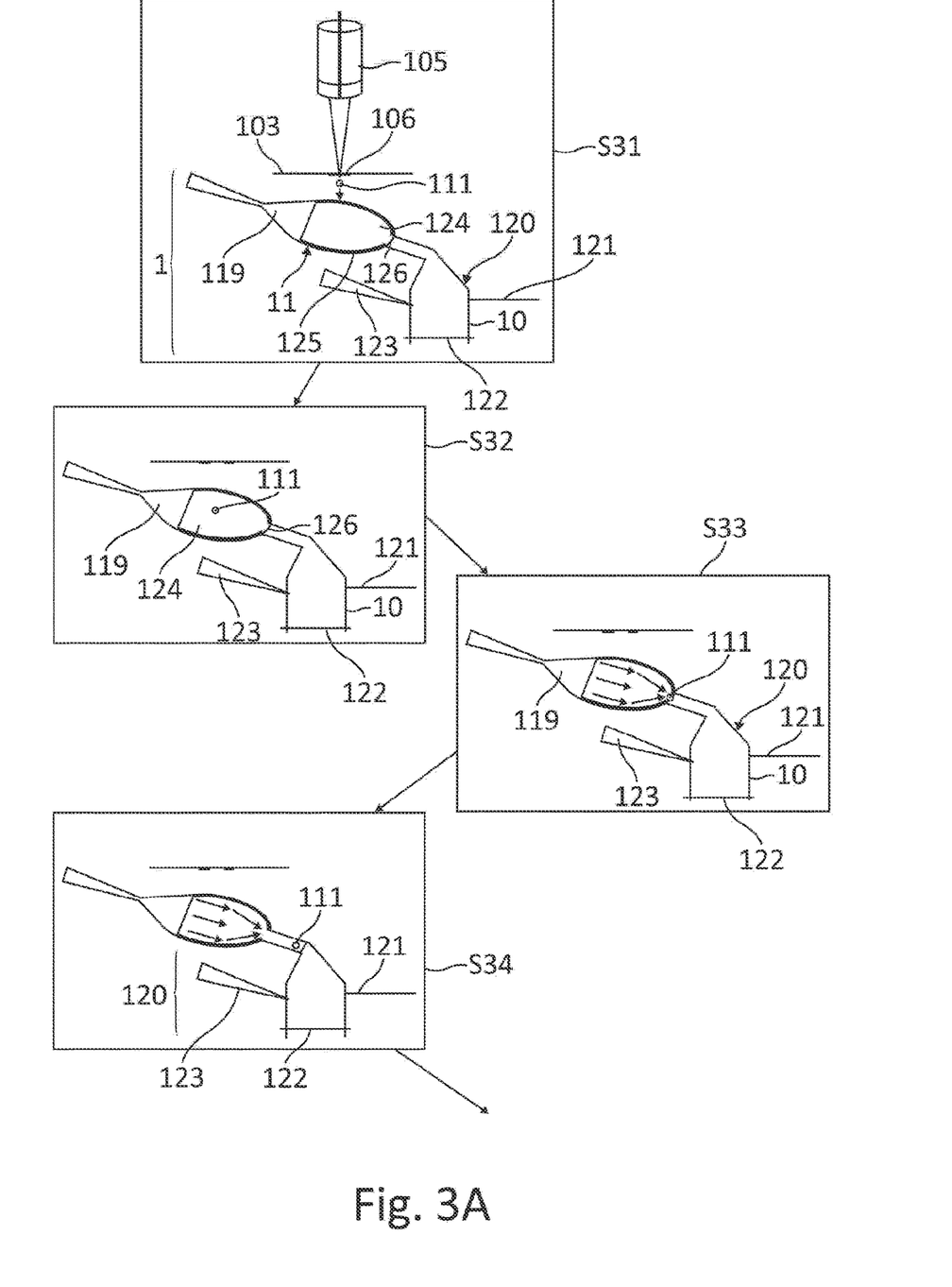
FIG. 3A shows a further alternative embodiment of the specimen collector according to the invention and first steps of the use thereof.
Figure 3B:
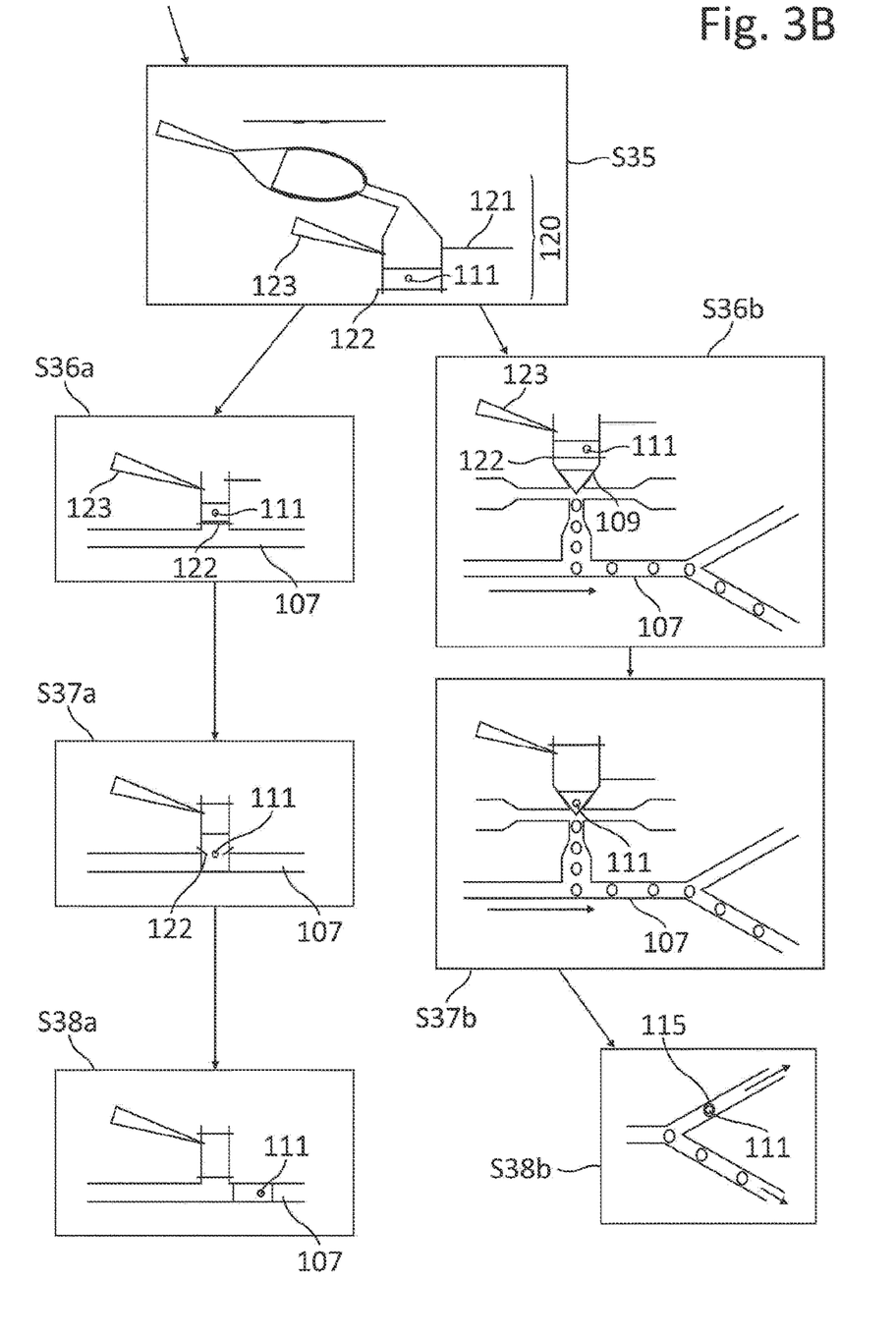
FIG. 3B shows further method steps in the use of a specimen collector shown in FIG. 3A.

FIGS. 3A and 3B show an alternative embodiment in which a collecting area 124 demarcated by raised side edges 125 is included upstream of the upper opening in the collecting chamber 10 of the specimen collector 1 as an outlet device 11. Said device preferably comprises a flushing or a discharge or suction device, with the aid of which a dissectate which has been collected can be sluiced to the discharge line 107.

In a first step S31 a dissectate 111 is detached here from a specimen 106 by laser microdissection. The dissectate falls downwards by means of gravity. In step S32 the dissectate is collected on the collecting area 124 of the outlet device 11 of the specimen collector 1. The collecting area 124 is inclined with respect to the horizontal. In the embodiment shown the outlet device 11 comprises an injector or a flushing device 119 with which a flushing liquid or another substance, generally a carrier substance, can be added. The side edges 125 of the collecting area 124 are raised in order to prevent (flushing) liquid from overflowing and to pass it to the outlet 126.

In the case shown, in step S32 still no liquid or other substance is passed into the collecting area 124. The collecting area 124 and the dissectate can therefore be inspected. Alternatively, the collecting area 124 can be wetted continuously by means of the flushing or the injector 119.

By flushing with a suitable flushing solution, the dissectate 111 is flushed through the outlet 126 in step S33, and in step S34 through a connection to the collecting chamber 10, which in the case shown is integrated into a capillary chamber 120. As an alternative to flushing, sucking up of the dissectate is conceivable.

The capillary chamber 120 shown comprises the actual collecting chamber 10, an intake valve 121, an exit valve 122 and an optional injector 123. Through the opened intake valve 121, in step S35 the dissectate 111 passes into the collecting chamber 10, the exit valve 122 of which is closed, as shown in FIG. 3B.

The collecting chamber 10 can be connected to a discharge line 107 directly (as shown in step S36a) or via a dispenser 109 (as shown in step S36b). If an injector 123 is present, in both cases one or more substance(s) can be added by said injector with the exit valve 122 closed.

Starting from step S36a (that is to say in the case where the collecting chamber 10 is not connected to a dispenser), in step S37a the exit valve 122 is opened and the dissectate is transferred into the discharge line 107, which here is a capillary. In step S38a the dissectate is fed in the surrounding liquid through the capillary 107 as shown, for example, in FIG. 1 to its further analysis. With respect to the further procedure, reference is made to FIG. 1 or FIGS. 2A and 2B.

In the case where the collecting chamber 10 is connected to a dispenser 109 (S36b), in steps S37b and S38b, analogously to steps S23b-S25 described for FIG. 2B, the dissectate is enclosed in a drop, which is separated from drops without dissectate and passed to a reaction site for analysis of the dissectate.

Figure 4:
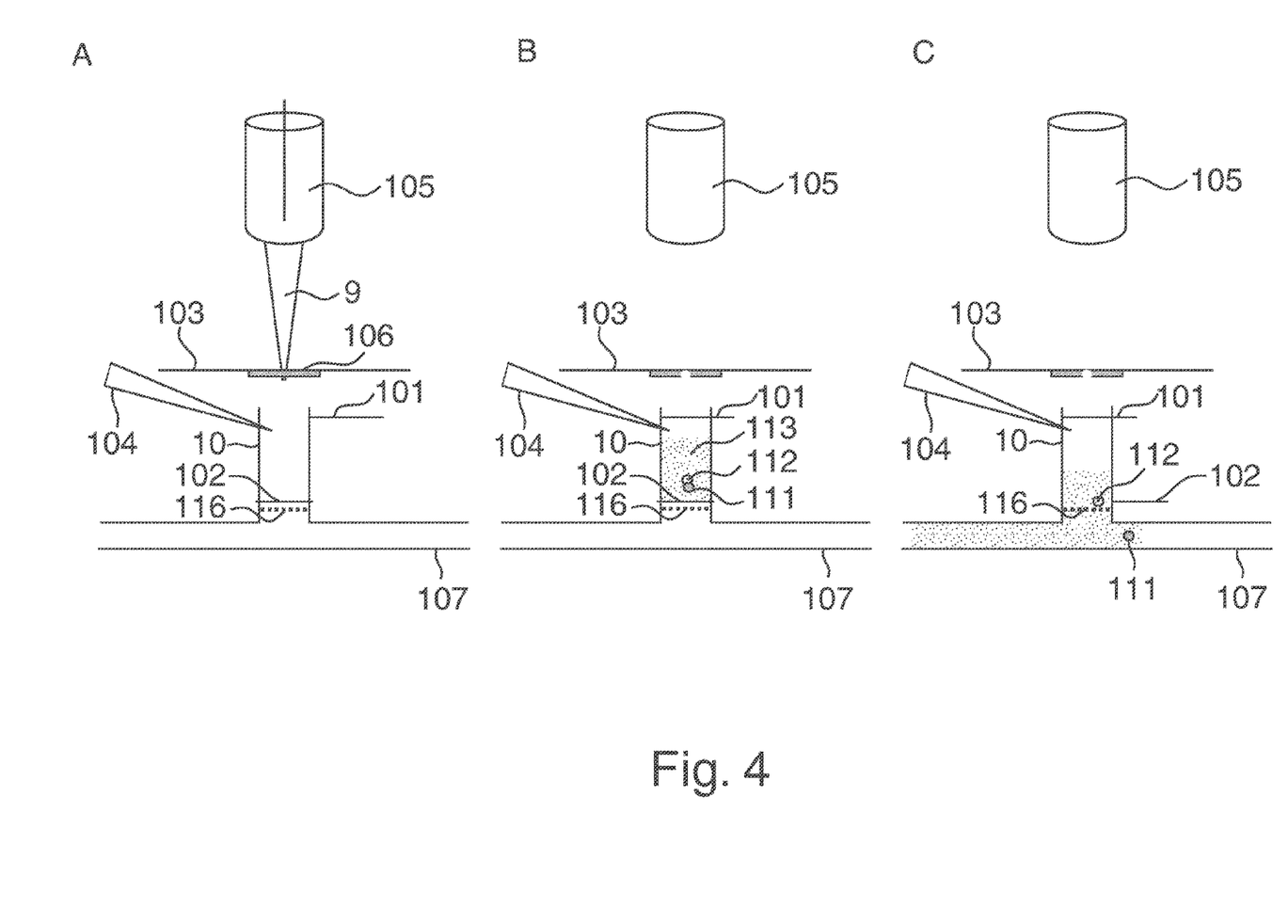
FIG. 4 shows a specimen collector with a filter system in various stages of use (FIG. 4A to 4C)

FIG. 4 shows the mode of functioning of an embodiment of a specimen collector 1 according to the invention such as is substantially already shown in FIG. 1, with a filter system for separating the dissectate 111 from substances 112 foreign to the dissectate, such as a membrane. For this, in FIG. 4 a filter 116 is arranged downstream of the first valve 102, the filter 116 still being arranged upstream the capillary line 107.

FIG. 4A shows a focusing lens 105 for a laser beam 9 which is focused on a specimen 106 held by a microscope slide 103. A dissectate which has been cut out falls into the collecting chamber 10 of the specimen collector 1 with the second valve 101 opened. In this respect reference is made to the explanations for FIG. 1.

A laser microdissection is as a rule performed with so-called membrane microscope slides. For this, the specimen 106 is applied to a suitable membrane (as a rule made of UV laser-absorbing material). The laser 9 of the laser microdissection system cuts a dissectate 111 out of the specimen 106, the membrane holding the dissectate 111 also being cut at the same time. As a result, the extracted specimen, that is to say the dissectate 111, is still joined to the similarly extracted membrane 112. This membrane 112 can block the capillaries of the capillary line 107 or influence subsequent reactions.

FIG. 4B shows the situation in the specimen collector 1 after the second valve 101 has been closed, after the dissectate 111 has fallen into the collecting chamber 10. A carrier substance 113 has already been added inside the collecting chamber 10 via the injector 104. The dissectate 111 is thus in the carrier liquid together with the membrane 12 with the first valve 102 closed. In the situation according to FIG. 4B the dissected specimen can be inspected. Lysis buffer which at least separates the dissectate 111 from the membrane fragment 112 or dissolves/lyses the specimen completely, while the membrane fragment 112 remains, can be added as the carrier substance 113.

FIG. 4C shows the situation after opening of the first (lower) valve 102. Since the filter 116 is permeable to the carrier substance (lysis buffer) 113 and to the dissectate 111 or the dissolved specimen, but on the other hand is impermeable to the membrane 112, the dissectate 111 is transferred into the capillary system 107, while the co-dissected membrane fragment 112 remains in the filter 116.

Figure 5:
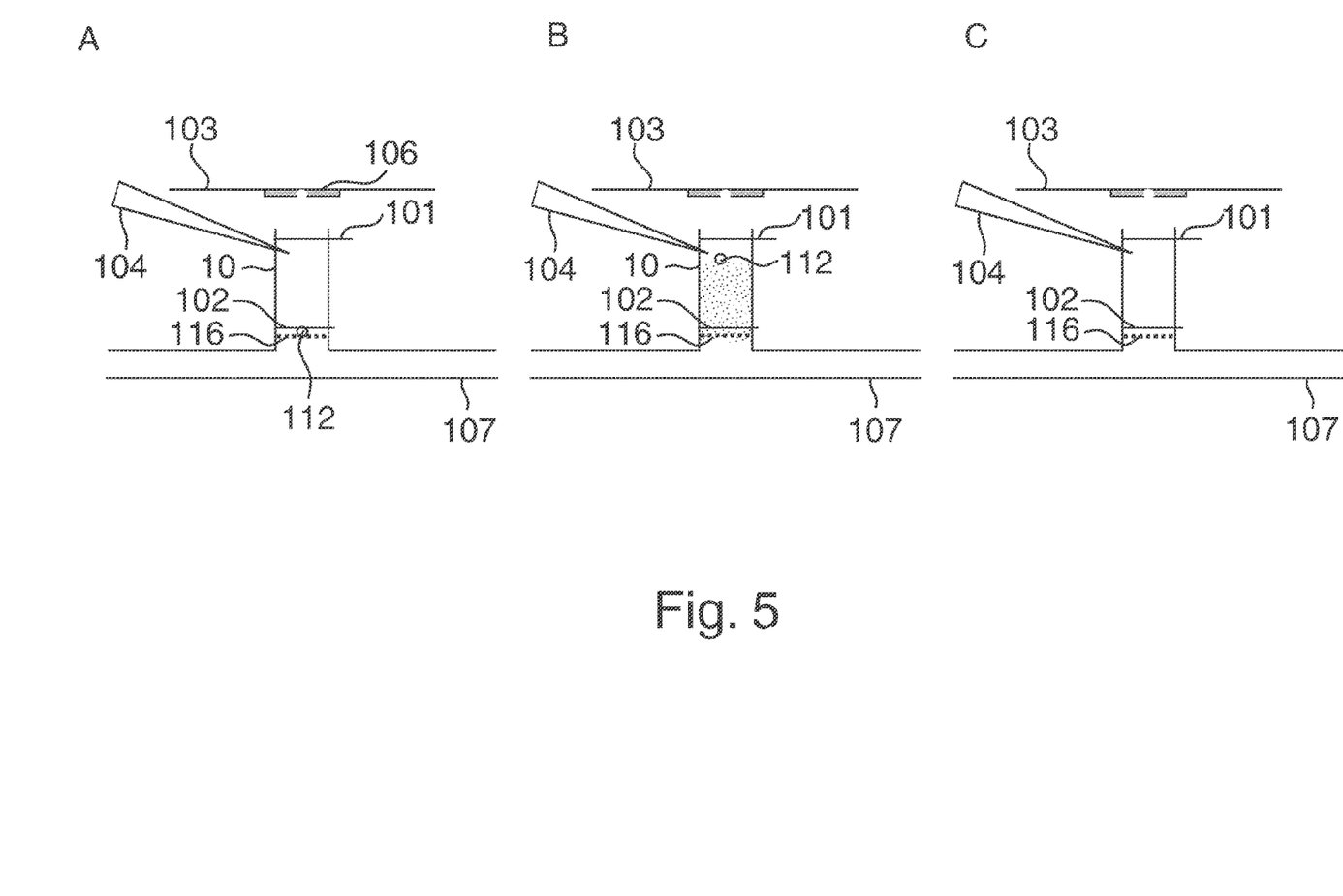
FIG. 5 shows possible cleaning of the filter system.

FIG. 5 schematically shows a possibility for cleaning the filter system.

In principle there are three possibilities for cleaning the filter system. Either the complete collecting chamber 10 with valves 101 and 102 and filter 116 can be exchanged, or only the filter 116, depending on the construction. In order to avoid such an exchange completely or at least to make it necessary only at relatively long intervals of time, the filter 116 can advantageously be washed out. This operation is schematically shown in FIG. 5A to 5C. The filter 116 is first washed out with the carrier substance or another filter cleaning liquid, so that with the valve 102 opened the filtered membrane 112 or several membrane fragments present there are flushed into the inside of the collecting chamber 10. The lower filter 102 is then closed again (see FIG. 5B). The inside of the collecting chamber 10 is now emptied, which can be effected by an injector arranged there, for example also the injector 104. It is also possible merely to suck off the membrane fragments 112 without completely emptying the collecting chamber 10. FIG. 5C shows the state after cleaning of the filter system. By opening the upper valve 101 the specimen collector is ready again to receive a dissectate.

FIG. 6 schematically shows a laser microdissection device such as can be employed for the present invention. A laser microdissection system which is particularly suitable for the present invention is described in detail in the German patent specification DE 10 2005 028 062 B4. With respect to certain details of this system which are mentioned in the following, reference is therefore made expressly to this specification, the disclosure of which in this respect is included in the present application.

The laser microdissection device 200 comprises a microscope 204 having a motorized x-y stage, the microscope stage 205, which serves to accommodate a microscope slide 103, to which is applied a preparation (specimen) 106 to be examined and/or to be cut. A transmitted light illumination device is designated 209. The specimen 106 can be illuminated in transmitted light and/or in incident light. A corresponding incident light device is designated 203. A corresponding light source of this incident light device 203 can be accommodated together with the laser light source 201. A separate arrangement, also with separate light paths, can also be employed. 206 designates a light source, such as a halogen lamp or a white-light LED, with a downstream illuminating lens for generating a transmitted light illumination beam path. This illumination beam path is directed onto the specimen 106 from underneath by means of a deflecting mirror 207 and a condenser 211. The microscope 204 furthermore comprises a lens 105 and microscope elements, such as a zoom system, tube lenses and eyepiece lenses. The eyepiece itself is designated 212.

The light of the transmitted light illumination beam path passing through the specimen collector 1 and the specimen 106 arrives at the lens 105, which records a section of the specimen 106 which can be viewed by an observer through the eyepiece 212 in the form of a microscope image. The microscope 204 is additionally connected to a camera 217, which can record a digital image of the preparation section, for example via a CCD chip. The image data received by the camera 217 are transmitted to a computer 220, which in turn is connected to a display surface 218 (monitor here), on which an image of the preparation section recorded can be shown. The computer 220 and camera 217 can completely or partly also form an integral unit.

The laser microdissection device 200 shown furthermore comprises a laser device (incident light device 203 here) for dissection of a laser microdissection region of the specimen 106 by laser cutting. For this, a laser light source 201 is coupled to the microscope 204, for example by joining the laser light source 201 to the microscope stand 208. The laser beam 9 generated by the laser light source 201 is coupled into the optical axis 210 of the microscope 204 via elements 216, 219, 214, 202 and 213, which are still to be explained, and focused via the objective lens 105 on the specimen 106 for cutting. By a relative movement between the laser beam 9 and specimen 106, the corresponding dissection region is then cut out of the preparation along a predetermined marking (cutting line). While this relative movement could be realised by appropriate movement of the microscope stage 205 and therefore of the microscope slide 103 with the laser beam 9 static, it is preferable and implemented in this embodiment to move the laser beam 9 with a static microscope stage 205 and static microscope slide 103 during the laser cutting. This has the great advantage that the specimen 106 can be observed directly during the laser microdissection.

For this purpose the laser beam 9 is guided via an (optional) attenuator unit 216 (attenuator), a focusing lens 219 and an aperture unit 214. By means of these elements a laser beam focus is generated at the desired place in the specimen 106 with the desired intensity and geometry in a known manner (see explicitly DE 10 2005 028 062 B4, which has already been mentioned). A deflecting element 213 serves to couple the laser beam 9 into the optical axis 210 of the microscope 204. A UV laser, for example, is suitable as the laser.

A control device is designated 215 in FIG. 6. It can comprise units separated from one another, as shown by way of illustration in FIG. 6, but in practice the control device is as a rule one unit, which in particular can also be integrated into the computer 220. In this embodiment the control device 215 is connected to the laser light source 201, the attenuator unit 216, the focusing lens 219, the aperture unit 214 and the deflecting device 202, which is still to be explained, in order to be able to control these elements in a suitable manner. A connection to the microscope stage 205 is also appropriate, in order to be able to move through or move up to various regions of the specimen 106. A connection to the camera 217 is likewise expedient, in order to be able to adjust recording parameters. With respect to further details, reference may again be made to DE 10 2005 028 062 B4.

To move the laser beam focus along a predetermined marking or cutting line for dissection of a specimen region (dissectate), a deflecting unit 202 is present, which comprises a pair of wedge plates, the individual wedge plates of which can be orientated relative to one another in a variable manner. In this manner, the laser beam can be deflected out of the optical axis by a displacement in a known manner, so that it impinges on the specimen 106 so as to be appropriately displaced, the laser beam passing through the centre of the lens pupil of the lens 105 for all deflection angles. For details with respect to the construction and mode of functioning of the deflecting device 202, reference is made expressly to the German patent specification DE 100 18 253 C2. By suitable control of the deflecting device 202, it is possible to guide the laser beam focus along any desired predetermined cutting line.

The laser microdissection device 200 described here allows recording of a specimen section, in particular with a fixed holding position of the microscope slide 103, by various microscope methods. The possible transmitted light illumination has already been explained above. The incident light device 203, explained here only for the laser device, is representative of other incident light illumination methods, such as contrasting methods or incident light fluorescence methods. It may be expedient to represent a preparation section with (at least) two different microscope methods, to overlay the microscope images and to define a cutting line (automatically or manually) in the overlaid image. The computer 220 then controls the deflecting device 202 via the control device 215 to generate a dissectate 111 from the specimen 106 in a corresponding manner. The dissectate 111 passes into the specimen collector 1 according to the invention, in particular into the inside of the collecting chamber 10.

The dissectate 111 present inside the collecting chamber 10 as already explained in detail with the aid of FIGS. 1 and 2 is transferred into a capillary line 107. A dispenser 109 (cf. FIG. 2) can also be provided for this. An outlet device 11, as explained in FIG. 3, can furthermore be employed. The dissectate 111 can be sorted out via a sorting intersection 108 (cf. FIG. 1) and fed to an analytical device. Excess carrier substance can be recycled via another line of the capillary system back to its origin (that is to say, for example, a reservoir, from where the carrier substance can be recycled back to its original site of use by means of a pump).

In order to be able to observe the operation of dissection microscopically, it is to be ensured that the elements of the specimen collector 1 in the transmitted light illumination beam path are largely transparent to light. Otherwise, observation in incident light can be selected. Transmitted light and incident light illumination as desired is also conceivable.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SYMBOLS

1 Specimen collector
9 Laser beam
10 Collecting chamber
11 Outlet device
101 First valve
102 Second valve
103 Microscope slide
104 Injector
105 Focusing lens, objective lens
106 Specimen
107 Discharge line, capillary line
108 Sorting intersection, branching
109 Dispenser
111 Dissectate
112 Membrane
113 Carrier substance
114 Substance addition
115 Drop
116 Filter
117 Capillary
118 Capillary
119 Flushing device
120 Capillary chamber
121 Second valve, intake valve
122 First valve, exit valve
123 Injector
124 Collecting area
125 Side edges
126 Outlet
200 Laser microdissection device
201 Laser light source
202 Deflecting device
203 Incident light device
204 Microscope
205 Microscope stage
206 Light source
207 Deflecting mirror
208 Microscope stand
209 Transmitted light illumination device
210 Optical axis
211 Condenser
212 Eyepiece
213 Deflecting element
214 Aperture unit
215 Control device
216 Attenuator unit
217 Camera
218 Display surface
219 Focusing lens
220 Computer
S11-S15 Method steps
S21-S26 Method steps
S31-S38b Method steps

The invention claimed is:

1. A laser microdissectate specimen collector for a laser microdissection device, the specimen collector comprising:
a collecting chamber configured to receive a microdissectate, the collecting chamber having, on a specimen side, an opening for receiving the microdissectate, the collecting chamber having a first valve, the first valve, in a closed state thereof, forming a closure of the collecting chamber opposite to the opening for retaining the microdissectate;
at least one of an injector or a dispenser disposed downstream of the opening and configured to provide a carrier substance to the microdissectate; and
a capillary line connected downstream of the first valve to the collecting chamber such that the capillary line is configured to transport the microdissectate out of the collecting chamber.

2. The specimen collector according to claim 1, wherein the collecting chamber has a second valve, the second valve, in a closed state thereof, forming a specimen-side closure of the collecting chamber.

3. The specimen collector according to claim 1, wherein the injector is configured to introduce the carrier substance into at least one of the collecting chamber and the capillary line.

4. The specimen collector according to claim 1, wherein the injector is arranged between the opening and the first valve of the collecting chamber.

5. The specimen collector according to claim 1, wherein the capillary line has a branching.

6. The specimen collector according to claim 1, wherein the dispenser is connected between the collecting chamber and the capillary line.

7. The specimen collector according to claim 1, further comprising an outlet device arranged upstream of the opening in the collecting chamber, an outlet of the outlet device being connected to the specimen-side opening of the collecting chamber.

8. The specimen collector according to claim 7, wherein the outlet device comprises at least one of a flushing device, a discharge device and a suction device.

9. The specimen collector according to claim 7, wherein the outlet device is configured as a collecting area demarcated by raised side edges.

10. The specimen collector according to claim 1, further comprising a filter connected downstream of the first valve and configured to allow the microdissectate to pass therethrough.

11. The specimen collector according to claim 10, wherein the filter is connected in a direction of flow before the capillary line.

12. The specimen collector according to claim 10, wherein the filter is configured to retain substances foreign to the microdissectate.

13. The specimen collector according to claim 10, wherein the filter is permeable to the carrier substance.

14. A laser microdissection device, comprising:
a laser light source configured to generate a laser beam;
a deflecting device configured to deflect the laser beam;
an objective lens;

an incident light device configured to focus the laser beam through the objective lens onto a specimen to be dissected;

a microscope stage configured to accommodate a microscope slide that holds the specimen; and a laser microdissectate specimen collector arranged on a specimen side of the microscope slide, the specimen collector comprising:

a collecting chamber configured to receive a microdissectate, the collecting chamber having, on the specimen side, an opening for receiving the microdissectate, the collecting chamber having a first valve, the first valve, in a closed state thereof, forming a closure of the collecting chamber opposite to the opening for retaining the microdissectate, the collecting chamber being disposed at a distance below the specimen such that the microdissectate will fall directly through the opening and into the collecting chamber after being cut by the laser beam;

at least one of an injector or a dispenser disposed downstream of the opening and configured to provide a carrier substance to the microdissectate; and a capillary line connected downstream of the first valve to the collecting chamber such that the capillary line is configured to transport the microdissectate out of the collecting chamber.

15. The microdissection device according to claim 14, wherein the collecting chamber has a second valve, the second valve, in a closed state thereof, forming a specimen-side closure of the collecting chamber.

16. The microdissection device according to claim 14, wherein the injector is configured to introduce the carrier substance into at least one of the collecting chamber and the capillary line.

17. The microdissection device according to claim 14, wherein the injector is arranged between the opening and the first valve of the collecting chamber.

18. The microdissection device according to claim 14, wherein the capillary line has a branching.

19. The microdissection device according to claim 14, wherein the dispenser is connected between the collecting chamber and the capillary line.

20. The microdissection device according to claim 14, further comprising an outlet device disposed upstream of the opening in the collecting chamber, an outlet of the outlet device being connected to the specimen-side opening in the collecting chamber.

21. The microdissection device according to claim 20, wherein the outlet device comprises at least one of a flushing device, a discharge device and a suction device.

22. The microdissection device according to claim 20, wherein the outlet device is configured as a collecting area demarcated by raised side edges.

23. The microdissection device according to claim 14, further comprising a filter connected downstream of the first valve and configured to allow the microdissectate to pass therethrough.

24. The microdissection device according to claim 23, wherein the filter is connected in a direction of flow before the capillary line.

25. The microdissection device according to claim 23, wherein the filter is configured to retain substances foreign to the microdissectate.

26. The microdissection device according to claim 23, wherein the filter is permeable to the carrier substance.

* * * * *